(12) United States Patent
Kaneko

(10) Patent No.: US 9,073,861 B2
(45) Date of Patent: Jul. 7, 2015

(54) DIPHENYLMETHYL PIPERAZINE DERIVATIVE AND PHARMACEUTICAL COMPOSITION USING SAME

(75) Inventor: Noboru Kaneko, Oyama (JP)

(73) Assignee: AETAS PHARMA CO., LTD., Tokyo (JP)

( * ) Notice: Subject to any disclaimer, the term of this patent is extended or adjusted under 35 U.S.C. 154(b) by 0 days.

(21) Appl. No.: 14/359,519

(22) PCT Filed: Jun. 15, 2012

(86) PCT No.: PCT/JP2012/003946
§ 371 (c)(1),
(2), (4) Date: May 20, 2014

(87) PCT Pub. No.: WO2013/099048
PCT Pub. Date: Jul. 4, 2013

(65) Prior Publication Data
US 2014/0296253 A1     Oct. 2, 2014

(30) Foreign Application Priority Data

Dec. 27, 2011 (JP) ................................ 2011-285970

(51) Int. Cl.
*A61K 31/496* (2006.01)
*C07D 211/52* (2006.01)

(52) U.S. Cl.
CPC ............ *C07D 211/52* (2013.01); *A61K 31/496* (2013.01)

(58) Field of Classification Search
None
See application file for complete search history.

(56) References Cited

U.S. PATENT DOCUMENTS

| 5,304,558 A | 4/1994 | Kaneko et al. | |
| 6,683,083 B1 * | 1/2004 | Kaneko et al. | 514/253.01 |

FOREIGN PATENT DOCUMENTS

| CN | 1058963 A | 2/1992 |
| JP | 4-69377 A | 3/1992 |
| JP | 2651043 B2 | 9/1997 |
| JP | 4152576 B2 | 9/2008 |

OTHER PUBLICATIONS

Cingolani et al., "Negative Lusitropic Effect of DPI 201-106 and E4031. Possible Role of Prolonging Action Potential Duration", Journal of Molecular and Cellular Cardiology, vol. 22, 1990, pp. 1025-1034.
Fraser et al., "Cardiovascular Effects of the Novel Cardiotonic Agent DPI 201-106 in the Anaesthetized Rat", Pharmacology & Toxicology, vol. 62, 1988, pp. 334-336.
Press et al., "Synthesis and SAR of 6-Substituted Purine Derivatives as Novel Selective Positive Inotropes", Journal of Medicinal Chemistry, vol. 35, No. 24, Nov. 27, 1992, pp. 4509-4515.
International Search Report dated Jul. 24, 2012 issued in corresponding application No. PCT/JP2012/003946.
Notification of Transmittal of Translation of the International Preliminary Report on Patentability (Form PCT/IB/338) of International Application No. PCT/JP2012/003946 mailed on Jul. 10, 2014, with Forms PCT/IB/373, PCT/ISA/237, and PCT/IB/326.
English Translation of Chinese Office Action dated Mar. 24, 2015, issued in corresponding Chinese Application No. 201280062663.5 (previously submitted Apr. 10, 2015) (7 pages).

* cited by examiner

*Primary Examiner* — Emily Bernhardt
(74) *Attorney, Agent, or Firm* — Westerman, Hattori, Daniels & Adrian, LLP

(57) ABSTRACT

The present invention provides: a novel compound which has a useful pharmacological action for treating heart failure or shock without increasing heart rate; and a pharmaceutical composition using the same. The present invention relates to a diphenylmethyl piperazine derivative represented by general formula (I)

[I]

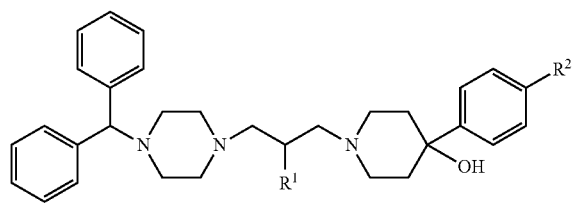

(In the formula, $R^1$ is a hydrogen atom or a hydroxy group. $R^2$ is a hydrogen atom, a halogen atom, a hydroxy group, an alkyl group having one to five carbon atoms, or an alkoxyl group having one to five carbon atoms, excluding the case where $R^1$ is a hydroxy group and $R^2$ is a chlorine atom.) or a pharmaceutically acceptable salt thereof, and a pharmaceutical composition containing the same.

8 Claims, 4 Drawing Sheets

DIPHENYLMETHYL PIPERAZINE DERIVATIVE AND PHARMACEUTICAL COMPOSITION USING SAME

TECHNICAL FIELD

The present invention relates to a diphenylmethyl piperazine derivative represented by the general formula [I] of the present invention or a pharmaceutically acceptable salt thereof, and a pharmaceutical composition comprising thereof.

BACKGROUND ART

The heart has a pumping function comprising periodic contraction and relaxation functions in the myocardium, which provides blood to the internal tissues and organs of the whole body and returns blood to the heart therefrom.

The heart contracts and relaxes regularly and periodically. This cardiac cycle is roughly divided into two phases; the systole and the diastole. The systole is from mitral valve closure to aortic valve closure and the diastole is from aortic valve closure to mitral valve closure. Further, the diastole consists of 4 phases; the isovolumetric relaxation phase, the rapid ventricular filling phase, the slow ventricular filling phase and the atrial contraction phase.

Among the four phases in the diastole, the initial first phase, which is the isovolumetric relaxation phase, is the beginning period of myocardial relaxation, and in the second to fourth phases of the diastole, blood flows from atrium to ventricle.

The cardiac function is separated into contractile (systolic) function and relaxing (diastolic) function. As a method for evaluating contractile and relaxing function, for the contractile function, the maximum +dP/dt, which is the first differential of left ventricular pressure in the left ventricular isovolumetric contraction phase, is used as an index. For the relaxing function, the maximum −dP/dt, which is the first differential of left ventricular pressure in the first phase of the four phases in the diastole, which is the isovolumetric relaxation phase, is used as an index of relaxing function. In addition, the left ventricular end-diastolic pressure is also used as an index of relaxing function, but is raised in both systolic heart failure and diastolic heart failure.

When the heart does not normally contract and relax, the pumping function is impaired and heart failure and shock occur.

The heart failure is developed when the contractile or relaxing/diastolic function is impaired. The symptoms are dyspnea, edema, tachycardia and the like. In addition, the heart failure is separated into systolic heart failure and diastolic heart failure depending on differences in developmental mechanisms, and cases in which cardiac contractile function is mainly impaired are called systolic heart failure, and cases in which relaxing/diastolic function is impaired are called diastolic heart failure.

Shock is a morbid state in which acute systemic circulatory failure is caused due to an acute decrease in blood pressure, and diagnosed using a systolic pressure of 90 mm Hg or less, oliguria, disturbance of consciousness, peripheral vasoconstriction and the like as criteria for diagnosis. The causes of shock include cardiogenic shock due to an acute impairment in cardiac function, and further hemorrhagic shock, septic shock, anaphylactic shock and the like.

The myocardial contractile and/or relaxing/diastolic function are impaired in heart failure and cardiogenic shock. When the myocardial contractile function is impaired, the +dP/dt decreases. On the other hand, when relaxing function is impaired, the maximum −dP/dt deteriorates (its absolute value decreases). When the left ventricular relaxing function is impaired, left ventricular end-diastolic pressure is raised.

The myocardial contractile and relaxing/diastolic function can be detected in the left ventricular myocardial wall motion by using Doppler echocardiography, and can be diagnosed by determining left ventricular pressure by using a pressure transducer-tipped catheter.

For treating heart failure and cardiogenic shock, cardiotonics are used in addition to treatment corresponding to causes thereof. Now, cardiotonic drugs include catecholamine formulations, phosphodiesterase inhibitors, calcium sensitizers, digitalis formulations, and the like. In heart failure and shock, cardiac rate increases. Catecholamine has the effect of raising cardiac rate, and cardiotonic drugs generally have a lethal arrhythmogenic effect to cause sudden death. These effects limit largely in treating heart failure and cargiogenic shock.

An agent having the effect of raising blood pressure and enhancing myocardial contraction and relaxation without increasing cardiac rate can make a desired medicine as a therapeutic agent for heart failure and shock. In addition, an agent having the effect of myocardial relaxation without increasing heart rate can make a medicine to improve relaxation impairment associated with ischemic heart disease, hypertensive heart disease or tachyarrhythmia.

It has been reported that certain types of diphenylmethyl piperazine derivatives prevent the development of myocardial necrosis and have an antitumor effect (see Patent Documents 1 and 2). There is, however, no description that these compounds have a vasopressor effect and the effect of enhancing myocardial contraction and relaxation herein.

CITATION LISTS

Patent Documents

Patent Document 1: JP 2651043 B2
Patent Document 2: JP 4152576 B2

SUMMARY OF INVENTION

Problems to be Solved by the Invention

The present invention provides novel compounds which have useful pharmacological effects for treating heart failure and shock by increasing blood pressure and enhancing the function of myocardial contraction and relaxation without increasing heart rate, and a pharmaceutical composition comprising thereof.

Means for Solving the Problems

The present inventors have examined a variety of pharmacological effects of diphenylmethyl piperazine derivatives. Thus, the present inventors found compounds, which have an extremely strong vasopressor effect and the effect of enhancing myocardial contraction and relaxation, among diphenylmethyl piperazine derivatives, and found that these compounds were derivatives which had extremely useful pharmacological effects to improve cardiac function.

That is, the present invention relates to a diphenylmethyl piperazine derivative represented by the following general formula [I]:

[Chemical Formula 1]

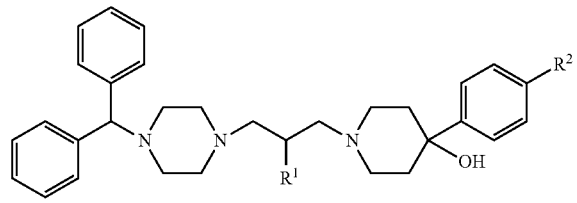

[I]

(wherein, $R^1$ represents a hydrogen atom or a hydroxy group, and $R^2$ represents a hydrogen atom, a halogen atom, a hydroxy group, an alkyl group having one to five carbon atoms, or an alkoxy group having one to five carbon atoms, excluding the case where $R^1$ is a hydroxy group and $R^2$ is a chlorine atom)
or a pharmaceutically acceptable salt thereof.

The present invention also relates to a pharmaceutical composition containing a diphenylmethyl piperazine derivative represented by the above formula [I] or a pharmaceutically acceptable salt thereof, and a pharmaceutically acceptable carrier.

More specifically, the present invention relates to the following [1] to [12].

[1] A diphenylmethyl piperazine derivative represented by the above general formula [I] or a pharmaceutically acceptable salt thereof.

[2] The diphenylmethyl piperazine derivative or the pharmaceutically acceptable salt thereof according to [1] above, wherein the diphenylmethyl piperazine derivative is represented below:

[Chemical Formula 2]

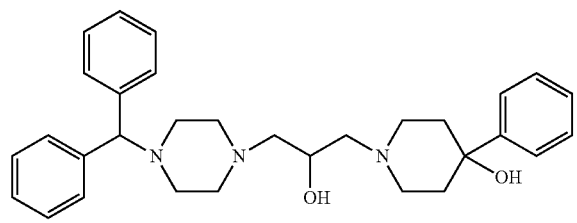

[2]

which is 1-[4-(diphenylmethyl)piperazinyl]-3-(4-hydroxy-4-phenyl-piperidinyl)-2-propanol (Compound [2]).

[3] The diphenylmethyl piperazine derivative or the pharmaceutically acceptable salt thereof according to [1] above, wherein the diphenylmethyl piperazine derivative is represented below:

[Chemical Formula 3]

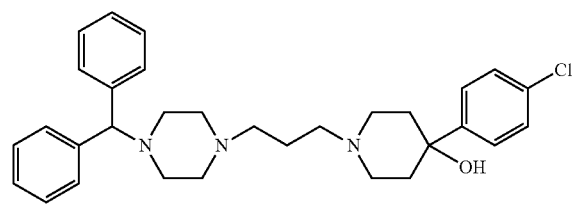

[3]

which is 1-[4-(diphenylmethyl)piperazinyl]-3-[4-(4-chlorophenyl)-4-hydroxy-piperidinyl]propane (Compound [3]).

[4] The diphenylmethyl piperazine derivative or the pharmaceutically acceptable salt thereof according to [1] above, wherein the diphenylmethyl piperazine derivative is represented below:

[Chemical Formula 4]

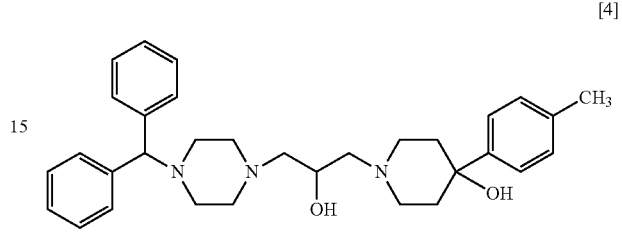

[4]

which is 1-[4-(diphenylmethyl)piperazinyl]-3-[4-hydroxy-4-(4-methylphenyl)-piperidinyl]-2-propanol (Compound [4]).

[5] The diphenylmethyl piperazine derivative or the pharmaceutically acceptable salt thereof according to any one of [1] to [4] above, wherein the pharmaceutically acceptable salt of the diphenylmethyl piperazine derivative is a salt selected from the group consisting of inorganic acid salts such as a hydrochloride, a sulfate, a nitrate, and a phosphate; and organic acid salts such as an oxalate, a malate, a citrate, a maleate, a fumarate, an adipate, a benzoate, a succinate, an acetate, and a tartrate.

[6] A pharmaceutical composition comprising the diphenylmethyl piperazine derivative or the pharmaceutically acceptable salt thereof according to any one of [1] to [5] above, and a pharmaceutically acceptable carrier.

[7] The pharmaceutical composition according to [6] above, wherein the pharmaceutical composition is a therapeutic or prophylactic agent for heart disease, or hypotension or shock other than heart disease.

[8] The pharmaceutical composition according to [7] above, wherein the heart disease is heart failure, cardiogenic shock, tachyarrhythmia, myocardial infarction, or angina pectoris.

[9] A method for treating heart disease, or hypotension or shock other than heart disease, the method comprising:
administering an effective amount of the diphenylmethyl piperazine derivative or the pharmaceutically acceptable salt thereof according to any one of [1] to [5] above to patients with heart disease, or hypotension or shock other than heart disease.

[10] The method according to [9] above, wherein the heart disease is heart failure, cardiogenic shock, tachyarrhythmia, myocardial infarction, or angina pectoris.

[11] The diphenylmethyl piperazine derivative or the pharmaceutically acceptable salt thereof according to any one of [1] to [5] above, which is used as a pharmaceutical composition for treatment or prevention of heart disease, or hypotension or shock other than heart disease.

[12] The diphenylmethyl piperazine derivative or the pharmaceutically acceptable salt thereof according to [11] above, wherein the heart disease is heart failure, cardiogenic shock, tachyarrhythmia, myocardial infarction, or angina pectoris.

Effects of the Invention

A compound represented by the general formula [I] of the present invention or a salt thereof per se has the effect of enhancing the function of myocardial contraction and relaxation and the effect of increasing blood pressure without increasing cardiac rate. Catecholamine formulations increase cardiac rate and increase oxygen consumption of the myocardium, while the compound of the present invention leads to lower oxygen consumption of the myocardium as compared to that of catecholamine formulations and does not increase cardiac rate unlike catecholamine formulations, and thus has useful properties for treatment of heart failure and cardiogenic shock.

A compound represented by the general formula [I] of the present invention or a salt thereof has the effect of enhancing the function of the left ventricular contraction and relaxation and has the effect of increasing blood pressure without increasing cardiac rate, and is extremely effective as a therapeutic or prophylactic agent for heart failure, cardiogenic shock, or hypotension or shock (hemorrhagic, septic and anaphylactic shock) other than heart disease.

Therefore, by the present invention, the treatment of cardiogenic shock and heart failure, which have been considered to be difficult to treat until now, get easier, and further there is provided a novel pharmaceutical composition as a therapeutic or prophylactic agent for shock, which is not caused by heart, such as hemorrhagic, septic and anaphylactic shock, and chronic heart failure.

In addition, a compound represented by the general formula [I] of the present invention or a salt thereof is provided as an active ingredient of a novel therapeutic or prophylactic agent for heart failure, cardiogenic shock, tachyarrhythmia, myocardial infarction, or angina pectoris.

Further, by using a compound represented by the general formula [I] of the present invention or a salt thereof in combination with other cardiotonics, the cardiac rate-increasing effect and arrhythmogenic effect of the other cardiotonics are decreased, and the amount of the other cardiotonics used can be reduced.

MODES FOR CARRYING OUT THE INVENTION

Figure 1:
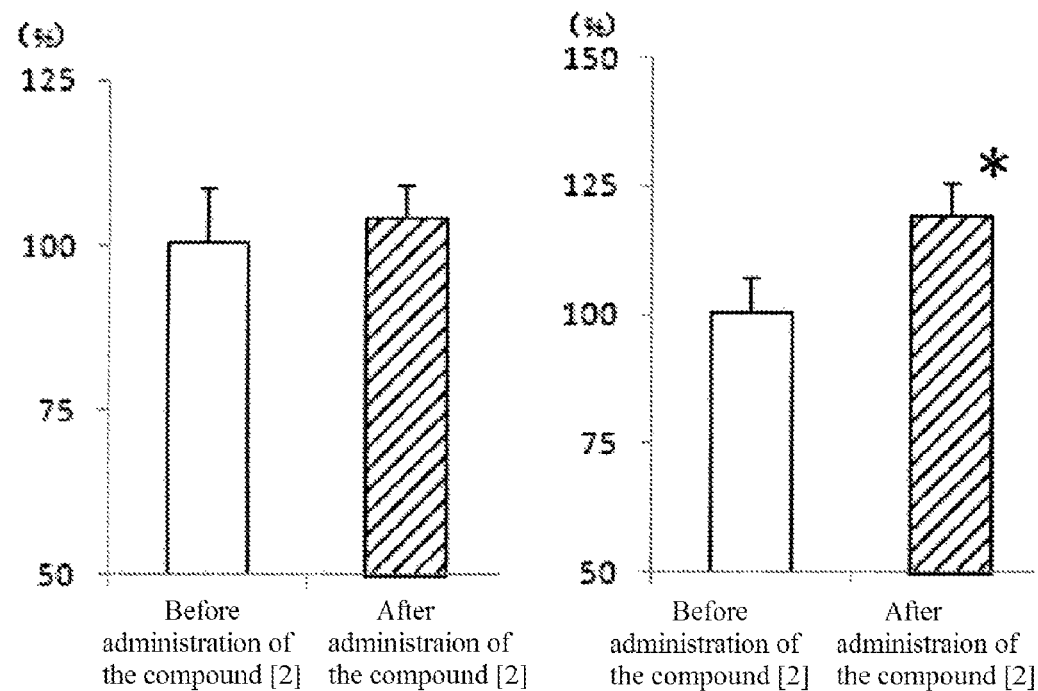
FIG. 1 shows graphs in which, when the compound [2] of the present invention is administered to normal rats, cardiac rate before and after administration (the left side in FIG. 1) and changes in left ventricular pressure before and after administration (the right side in FIG. 1) are compared. The * sign in FIG. 1 indicates that there is a significant difference between pre-administration of the compound [2] and post-administration at $p<0.05$.

The present invention relates to the compounds of the present invention, that is, diphenylmethyl piperazine derivatives represented by the following general formula [I]:

[Chemical Formula 5]

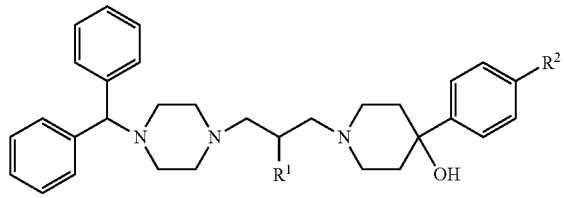

[I]

(wherein, $R^1$ represents a hydrogen atom or a hydroxy group, and $R^2$ represents a hydrogen atom, a halogen atom, a hydroxy group, an alkyl group having one to five carbon atoms, or an alkoxy group having one to five carbon atoms, excluding the case where $R^1$ is hydroxy group and $R^2$ is a chlorine atom) or a pharmaceutically acceptable salt thereof.

The halogen atoms in the present invention include a fluorine atom, a chlorine atom, a bromine atom, and the like. Preferred halogen atoms in the present invention include a chlorine atom.

The alkyl groups having one to five carbon atoms in the present invention include a straight or branched alkyl group having one to five carbon atoms, preferably one to three carbon atoms. Preferred examples of alkyl groups having one to five carbon atoms in the present invention include a methyl group, an ethyl group, and the like.

The alkoxy groups having one to five carbon atoms in the present invention include an alkoxy group constituted from the above alkyl group having one to five carbon atoms, preferably one or two carbon atoms. Preferred examples of alkoxy groups having one to five carbon atoms in the present invention include a methoxy group, an ethoxy group, and the like.

As preferred examples of compounds represented by the general formula [I] of the present invention, when $R^1$ is a hydroxy group, $R^2$ is a hydrogen atom, and when $R^1$ is a hydrogen atom, $R^2$ can be any of a hydrogen atom, a halogen atom, a hydroxy group, an alkyl group having one to five carbon atoms, or an alkoxy group having one to five carbon atoms. When $R^1$ is a hydrogen atom, $R^2$ is preferably a halogen atom, an alkyl group having one to five carbon atoms, or an alkoxy group having one to five carbon atoms. $R^2$ is particularly preferably a halogen atom, and is further preferably a chlorine atom.

Among compounds represented by the general formula [I] of the present invention, as particularly preferred examples of the compounds, the compound [2] represented by the following formula:

[Chemical Formula 6]

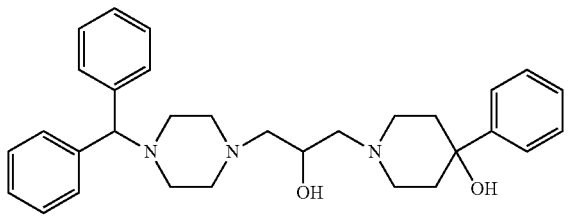

[2]

the compound [3] represented by the following formula:

[Chemical Formula 7]

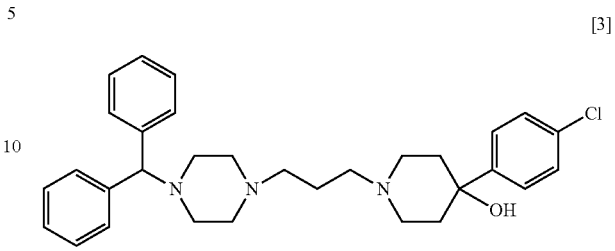

[3]

and the compound [4] represented by the following formula:

[Chemical Formula 8]

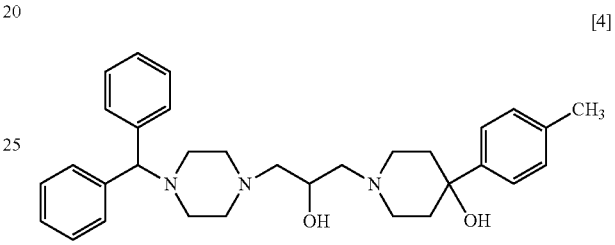

[4]

are mentioned.

Examples of pharmaceutically acceptable salts of a diphenylmethyl piperazine derivative represented by the general formula [I] of the present invention include inorganic acid salts such as a hydrochloride, a sulfate, a nitrate, and a phosphate; organic acid salts such as an oxalate, a malate, a citrate, a maleate, a fumarate, an adipate, a benzoate, a succinate, an acetate, and a tartrate; and the like.

In addition, when these compounds of the present invention form solvates such as hydrates, these solvates are also encompassed in the compounds of the present invention.

A diphenylmethyl piperazine derivative represented by the general formula [I] of the present invention or a pharmaceutically acceptable salt thereof can be produced according to a known method. Specific production method includes a method described in examples described below.

A compound in which $R^1$ is a hydroxy group, for example, can be produced by reacting halohydrin and diphenylmethyl piperazine to obtain a corresponding epoxy body and then reacting the obtained epoxy body and substituted or unsubstituted 4-hydroxy-4-phenyl-piperidine according to a known method. The epoxy body, an intermediate, can be produced by a known method.

A compound in which $R^1$ is a hydrogen atom in the general formula [I] can be produced using a propane derivative having two types of leaving groups such as 1,3-dihalopropane in place of halohydrin in the above method by the similar method as described above.

Both of these methods are methods by a substitution reaction and can be carried out according to known reaction conditions in substitution reactions.

A compound represented by the general formula [I] of the present invention or a salt thereof is useful as an active ingredient of a therapeutic or prophylactic agent for heart disease, heart failure and shock, and is particularly useful as an active ingredient of a therapeutic or prophylactic agent for heart disease, heart failure and shock by enhancing the function of myocardial contraction and relaxation without increasing cardiac rate.

Therefore, a compound represented by the general formula [I] of the present invention or a salt thereof can be used as an active ingredient of a pharmaceutical composition. The pharmaceutical composition of the present invention is only required to contain a diphenylmethyl piperazine derivative represented by the general formula [I] of the present invention or a pharmaceutically acceptable salt thereof as an active ingredient, and by further using a β-blocker and an angiotensin receptor blocker (ARB), which are therapeutic medicines for heart failure, in combination as an active ingredient, the amount of β-blocker and $Ca^{2+}$ antagonist used can be reduced, and thus such case can be also mentioned as a preferred example of the pharmaceutical composition of the present invention.

The pharmaceutical composition of the present invention can be administered orally or parenterally, for example, sublingually, intraorally, in the patch form, intravenously, intraocularly and the like.

When a formulation for oral administration is made using the pharmaceutical composition of the present invention, dosage forms such as a tablet, a pill, powders, and a granule can be used. In such dosage forms, one or more active substances (active ingredient) are mixed with at least one pharmaceutically acceptable carrier which is inactive, such as a diluent, a dispersing agent or an adsorbent, such as lactose, mannitol, glucose, hydroxypropyl cellulose, microcrystalline cellulose, starch, polyvinyl pyrrolidone, magnesium aluminometasilicate or silicic anhydride powder, and a formulation can be formed according to a conventional method.

When a tablet or a pill is prepared, it can be coated with a film of a gastrosoluble or liposoluble substance such as white soft sugar, gelatin, hydroxypropyl cellulose or hydroxymethyl cellulose phthalate, or can be coated with two or more layers as needed. Further, a capsule can be made using a substance as gelatin or ethyl cellulose.

When a liquid composition for oral administration is made, a dosage form such as a pharmaceutically acceptable emulsion, resolvent, suspension, syrup, or elixir can be used. A diluent to be used is, for example, purified water, ethanol, vegetable oil, an emulsifier, or the like. In addition, this composition can be mixed with an adjuvant such as a humectant, a suspending agent, a sweetening agent, a flavoring agent, a perfume or an antiseptic in addition to a diluent.

When an injection product for parenteral administration is prepared, a sterile aqueous or nonaqueous solution, a solubilizing agent, a suspending agent, or an emulsifier is used. The aqueous solution, solubilizing agent, and suspending agent are, for example, water for injection, distilled water for injection, physiological saline, cyclodextrin and derivatives thereof, organic amines such as triethanolamine, diethanolamine, monoethanolamine and triethylamine, an inorganic alkali solution or the like.

When a water-soluble solution is made, for example, propylene glycol, polyethylene glycol or vegetable oil such as olive oil, alcohols such as ethanol and the like can be used.

In addition, for example, a surfactant such as polyoxyethylene hydrogenated castor oil or sucrose fatty acid ester (mixed micellization), or lecithin or hydrogenated lecithin (liposome formation) or the like is used as a solubilizing agent. In addition, an emulsion formulation having a water-insoluble resolvent such as vegetable oil, and lecithin, polyoxyethylene hydrogenated castor oil, polyoxyethylene polyoxypropylene glycol or the like can be made.

A compound represented by the general formula [I] of the present invention or a salt thereof can be orally or parenterally administered as a free compound in a range of normally 0.01 mg to 1 g/kg per adult divided into one to several times daily, which varies depending on age, body weight, symptoms, therapeutic effect, administration route, treatment time and the like.

EXAMPLES

The present invention will be now described in more detail by way of examples of the present invention. It should be noted, however, that the present invention is not limited by exemplification and explanation herein.

Example 1

The compound [2] of the present invention, 1-[4-(diphenylmethyl)piperazinyl]-3-(4-hydroxy-4-phenyl-piperidinyl)-2-propanol, was produced according to the following reaction path.

[Chemical Formula 9]

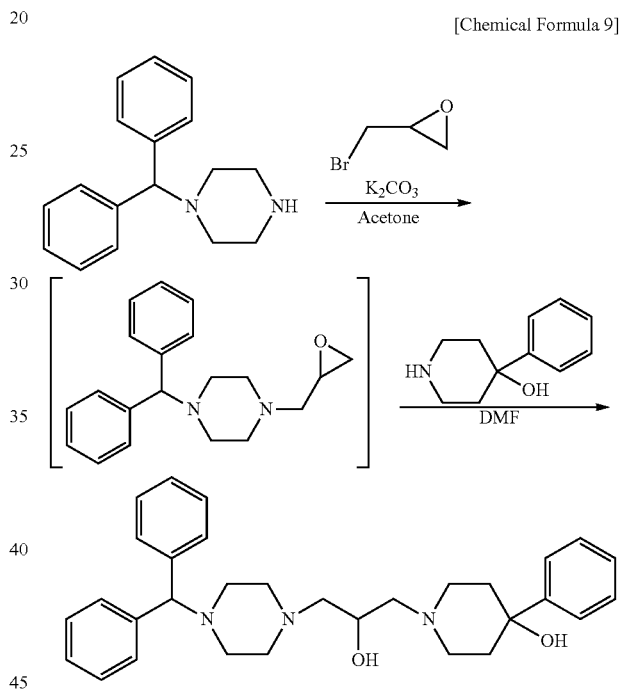

(1) Production of an Epoxy Body

In acetone, 1-(diphenylmethyl)piperazine (6.0 g) was dissolved (20 v/w), and potassium carbonate (1.5 eq.) and epibromohydrin (2.0 eq.) were added thereto, and the obtained mixture was heated to reflux for 3.5 hours. The salt produced by the reaction was separated by filtration, and the filtrate was then concentrated in vacuo to obtain a crude product of 1-(diphenylmethyl)-4-(1-(2,3-epoxy)propyl)piperazine.
$^1$H-NMR (CDCl$_3$, 400 MHz) δ:
2.27-2.74 (12H, m), 3.06 (1H, m), 4.21 (1H, s), 7.15 (2H, t), 7.23 (4H, t), 7.39 (4H, d)

(2) Production of 1-[4-(diphenylmethyl)piperazinyl]-3-(4-hydroxy-4-phenyl-piperidinyl)-2-propanol (compound [2])

A solution of the total crude product produced in the above (1), 1-(diphenylmethyl)-4-(1-(2,3-epoxy)propyl)piperazine, and 4-hydroxy-4-phenyl-piperizine (1.3 eq.) in DMF (14 v/w) was dissolved in DMF (20 v/w), and the obtained solution was heated to reflux at 100° C. for 10 hours. The solution was allowed to cool and then concentrated, and purified by silica gel column chromatography (Wakogel C-200, 100 g) to obtain 4.9 g of 1-[4-(diphenylmethyl)piperazinyl]-3-(4-hydroxy-4-phenyl-piperidinyl)-2-propanol, which is a target compound, as a white solid.

IR ν max (cm$^{-1}$) KBr:
3385, 2952, 2807, 1598, 1492, 1449, 1138, 758, 700
$^1$H-NMR (CDCl$_3$, 400 MHz) δ:
1.53-2.87 (21H, m), 3.88 (2H, m), 4.22 (1H, s), 7.15-7.52 (15H, m)
FD-MS (m/z):
Found value 486.8 (M$^+$) as $C_{31}H_{39}N_3O_2$ Example 2

In addition, the compound [3] of the present invention, 1-[4-(diphenylmethyl)piperazinyl]-3-[4-(4-chlorophenyl)-4-hydroxy-piperidinyl]propane, was produced according to the following reaction path.

[Chemical Formula 10]

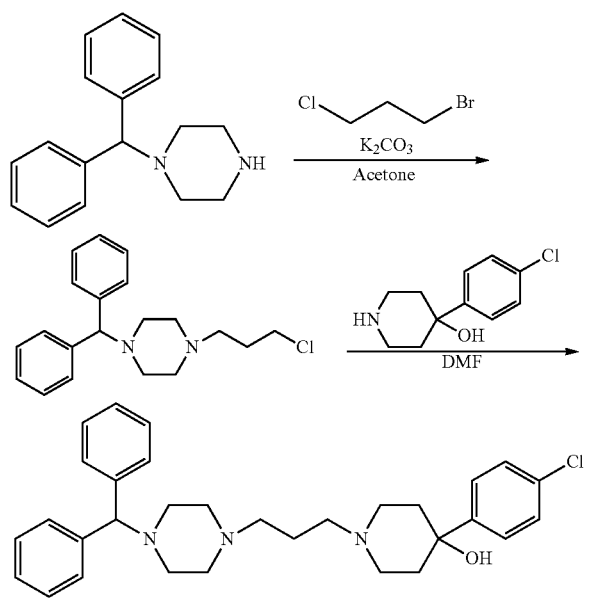

(1) Production of 1-[4-(diphenylmethyl)piperazinyl]-3-chloropropane

In acetone, 1-(diphenylmethyl)piperazine (18.49 g) was dissolved, and potassium carbonate (1.0 eq.) and 1-bromo-3-chloropropane (2.0 eq.) were added thereto, and the obtained mixture was heated to reflux for 3 hours. The salt produced by the reaction was separated by filtration, and the filtrate was then concentrated in vacuo. The residue was purified by silica gel column chromatography (Wakogel C-200, 200 g) and eluted by a mixed solvent of 99 parts of chloroform and 1 part of methanol to obtain 1-[4-(diphenylmethyl)piperazinyl]-3-chloropropane (13.8 g).

$^1$H-NMR (CDCl$_3$, 400 MHz) δ:
1.9 (2H, m), 2.35 (10H, m), 3.45 (2H, t), 4.15 (1H, s), 7.2 (10H, m)

(2) Production of 1-[4-(diphenylmethyl)piperazinyl]-3-[4-(4-chlorophenyl)-4-hydroxy-piperidinyl]propane In DMF, 9.0 g of 1-[4-(diphenylmethyl)piperazinyl]-3-chloropropane (2.0 eq) and 4-(4-chlorophenyl)-4-hydroxypiperidine (2.0 eq.) were dissolved (20 v/w), and the obtained solution was heated to reflux at 80° C. for 6 hours. The solution was allowed to cool and then concentrated, and purified by silica gel column chromatography (Wakogel C-200, 100 g) to obtain 8.3 g of 1-[4-(diphenylmethyl)piperazinyl]-3-[4-(4-chlorophenyl)-4-hydroxy-piperidinyl]propane (yield 60.1%), which is a target compound, as a white solid in an amorphous state.

IR ν max(cm$^{-1}$) KBr:
3166, 2946, 2809, 1596, 1492, 1450, 1143, 758, 706
$^1$H-NMR (CDCl$_3$, 400 MHz) δ:
1.60-1.70 (4H, m), 1.90-2.20 (3H, m), 2.30-2.70 (14H, m), 2.80-2.90 (2H, D), 4.20 (1H, s), 7.10-7.50 (14H, m)
FD-MS (m/z):
Found value 503 (M$^+$) as $C_{31}H_{38}N_3OCl$ Example 3

In addition, the compound [4] of the present invention, 1-[4-(diphenylmethyl)piperazinyl]-3-[4-hydroxy-4-(4-methylphenyl)-piperidinyl]-2-propanal, was produced according to the following reaction path.

[Chemical Formula 11]

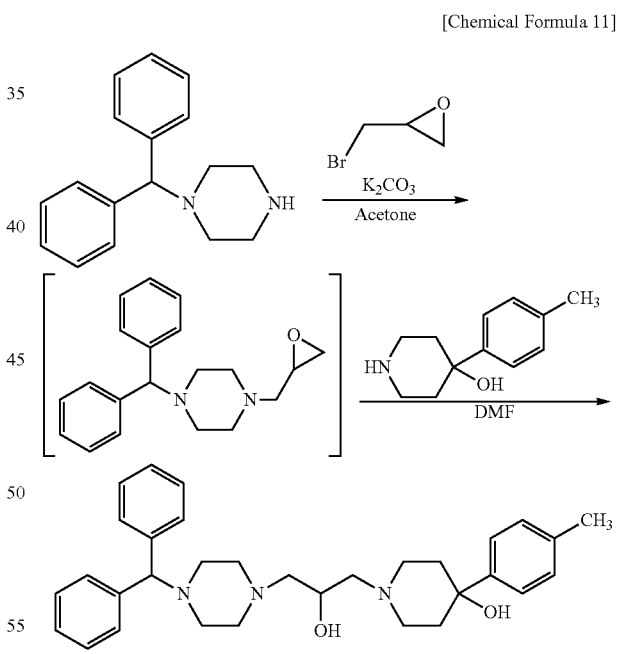

(1) Production of an Epoxy Body

Based on the method described in Example 1 (1) described above, 1-(diphenylmethyl)-4-(1-(2,3-epoxy)propyl)piperazine was obtained.

$^1$H-NMR (CDCl$_3$, 400 MHz) δ:
2.27-2.74 (12H, m), 3.06 (1H, m), 4.21 (1H, s), 7.15 (2H, t), 7.23 (4H, t), 7.39 (4H, d)

(2) Production of 1-[4-(diphenylmethyl)piperazinyl]-3-[4-hydroxy-4-(4-methylphenyl)-piperidinyl]-2-propanol (compound [4])

In DMF (140 mL), 1-(diphenylmethyl)-4-(1-(2,3-epoxy) propyl)piperazine (14.0 g) produced in the above (1) and 4-hydroxy-4-(4-methylphenyl)-piperidine (13.0 g) were dissolved, and the obtained solution was heated to reflux at 100° C. for 3 hours. The solution was allowed to cool and then concentrated, and purified by silica gel column chromatography (Wakogel C-200, 100 g) to obtain 15.7 g of 1-[4-(diphenylmethyl)piperazinyl]-3-[4-hydroxy-4-(4-methylphenyl)-piperidinyl]-2-propanol, which is a target compound, as a white solid.

IR ν max ($cm^{-1}$) KBr:
3438, 2942, 2815, 1639, 1492, 1451, 1137, 1007, 816, 746, 706

$^1$H-NMR (CDCl$_3$, 400 MHz) δ:
1.64-2.85 (21H, m), 2.33 (3H, s), 3.89 (2H, m), 4.21 (1H, s), 7.15-7.42 (14H)

Example 4

Test Example 1

Comparison of Hemodynamics Before and after Administration of the Compound [2] of the Present Invention Wistar male rats were bred for a week and then anesthetized by inhalation of 3% isoflurane. A pressure sensor-tipped catheter (2F Millar) was inserted into the left ventricle from the right common carotid artery, and a polyethylene tube (SP10) for injection of the compounds of the present invention or physiological saline was inserted from the right femoral vein. After stabilizing hemodynamics for 10 minutes, the compound [2] of the present invention was administered from the polyethylene tube at 0.1 mg/kg/min for 10 min, and the cardiac rate, left ventricular pressure, maximum +dP/dt, and maximum −dP/dt were measured for 20 heart beats every minute. In the control group, only physiological saline, which is a solvent, was administered. It is noted that the injection rate of each solution was 16.6 μl per min.

Figure 2:
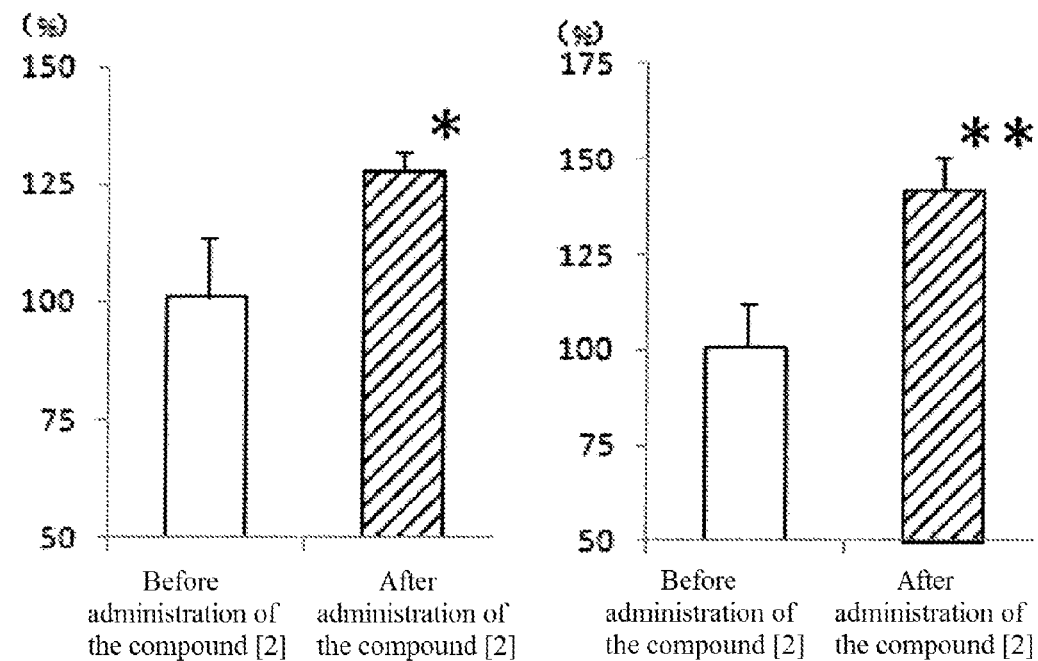
FIG. 2 shows graphs in which, when the compound [2] of the present invention is administered to normal rats, the maximum +dP/dt which is an index of contractile function before and after administration (the left side in FIG. 2) and the maximum −dP/dt which is an index of relaxing function before and after administration (the right side in FIG. 2) are compared. The * sign in FIG. 2 indicates that there is a significant difference between pre-administration of the compound [2] and post-administration at $p<0.05$. The ** sign indicates that there is a significant difference between pre-administration of the compound [2] and post-administration at $p<0.01$.

The cardiac rate, maximum left ventricular pressure, maximum +dP/dt and maximum −dP/dt before administration of a drug were considered as 100%, and the values after administration were represented by values (% representation) relative to the values before administration. Using n=3 rats, experiments were carried out. Data are shown as mean and standard deviation. Consequently, cardiac rate before and after administration (the left side in FIG. 1) and changes in the maximum left ventricular pressure (the right side in FIG. 1) are shown in FIG. 1, and changes in the maximum +dP/dt (the left side in FIG. 2) and changes in the maximum −dP/dt (the right side in FIG. 2) are shown in FIG. 2.

Thus, by administration of the compound [2] of the present invention, the cardiac rate was not increased, the left ventricular pressure was significantly raised, and significant increases in the maximum +dP/dt and the maximum −dP/dt were observed in normal rats. In the control group, significant changes were not observed before and after administration of only physiological saline, which is a solvent. From this result, it was found that the compound [2] of the present invention raised blood pressure without increasing cardiac rate, and had the effect of enhancing the function of myocardial contraction and relaxation.

Test Example 2

About the Influence of the Compound [2] of the Present Invention on the Effect of Myocardial Contraction and Relaxation of Rats with Obsolete Myocardial Infarction Wistar male rats were anesthetized by inhalation of 3% isoflurane. The chest was opened at the left third intercostal space and the pericardial membrane was incised. The left anterior descending coronary artery was completely ligated with silk string (6.0; Ethicon) in the infarction group, and then the chest was immediately closed. Following this procedure, the inserted endotracheal tube was removed, and rats were awakened and then returned to a breeding room.

One month after operation, rats were anesthetized and endotracheally intubated, a pressure sensor-tipped catheter (2F Millar) was inserted into the left ventricle from the right common carotid artery, and a polyethylene tube (SP10) for injection of physiological saline or the compounds of the present invention was inserted from the right femoral vein in the same manner as in Test Example 1. After stabilizing hemodynamics for 10 minutes, the compound [2] of the present invention was administered from the polyethylene tube at 0.1 mg/kg/min for 10 min, and the cardiac rate, left ventricular pressure, maximum +dP/dt, and maximum −dP/dt were measured for 20 heart beats every minute. In the control group, only physiological saline, which is a solvent, was administered. It is noted that the injection rate of each solution was 16.6 μl per min. Using n=3 rats, experiments were carried out.

Figure 3:
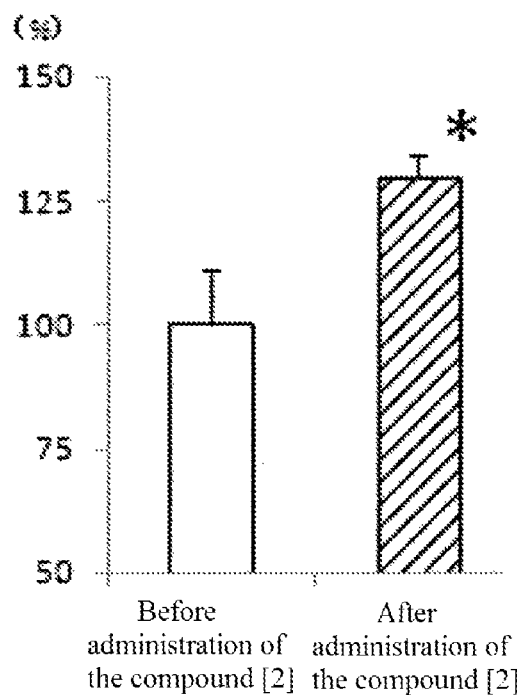
FIG. 3 shows graphs in which, when the compound [2] of the present invention is administered to rats with obsolete myocardial infarction, the maximum +dP/dt which is an index of contractile function before and after administration (the left side in FIG. 3) and the maximum −dP/dt which is an index of relaxing function before and after administration (the right side in FIG. 3) are compared. The * sign in FIG. 3 indicates that there is a significant difference between pre-administration of the compound [2] and post-administration at $p<0.05$. The ** sign indicates that there is a significant difference between pre-administration of the compound [2] and post-administration at $p<0.01$.
Figure 3:
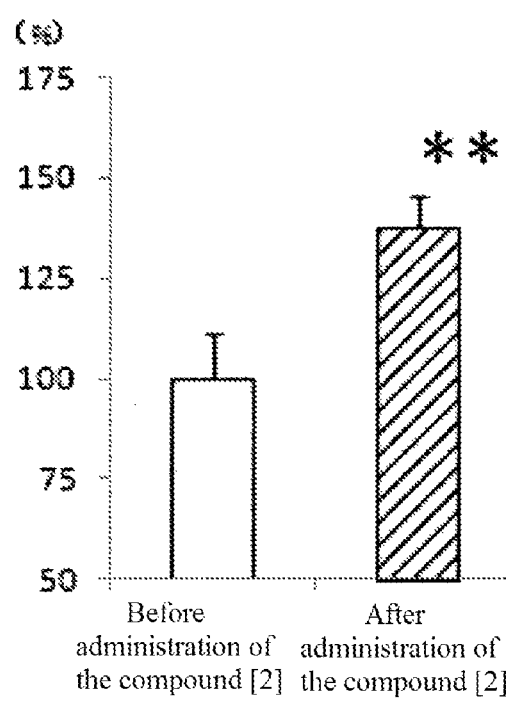

The maximum +dP/dt or the maximum −dP/dt before administration was considered as 100%, and the value after administration was represented by a value (% representation) relative to the value before administration. The result is shown in FIG. 3. Data are shown as mean and standard deviation.

Thus, as is the case with Test Example 1, significant changes in the cardiac rate were not observed, and the left ventricular pressure was significantly increased as compared to that before administration of the compound [2] of the present invention. In addition, as shown in FIG. 3, the maximum +dP/dt (the left side in FIG. 3) and the maximum −dP/dt (the right side in FIG. 3) were also significantly increased by administration of the compound [2] of the present invention in the obsolete myocardial infarction cases.

Thus, it was found that the compound [2] of the present invention also had the effect of enhancing the myocardial contraction and relaxation in the diseased heart.

Test Example 3

Figure 4:
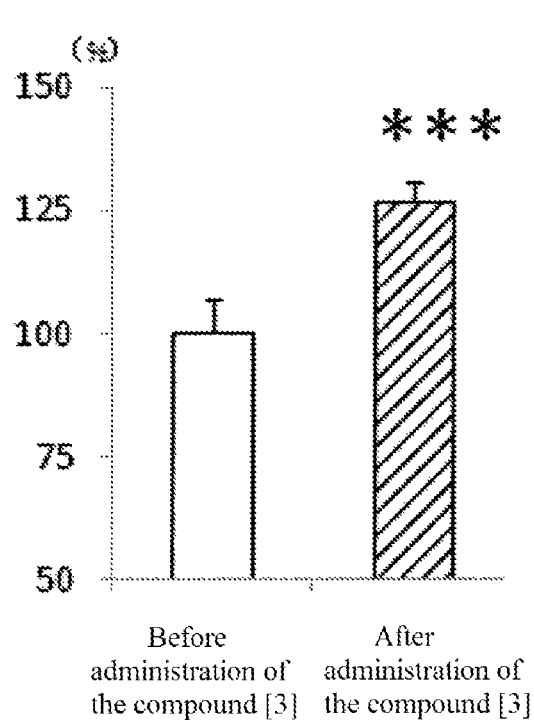
FIG. 4 shows graphs in which, when the compound [3] of the present invention is administered to normal rats, the maximum +dP/dt which is an index of contractile function before and after administration (the left side in FIG. 4) and the maximum −dP/dt which is an index of relaxing function before and after administration (the right side in FIG. 4) are compared. The *** sign in FIG. 4 indicates that there is a significant difference between pre-administration of the compound [3] and post-administration at $p<0.005$.
Figure 4:
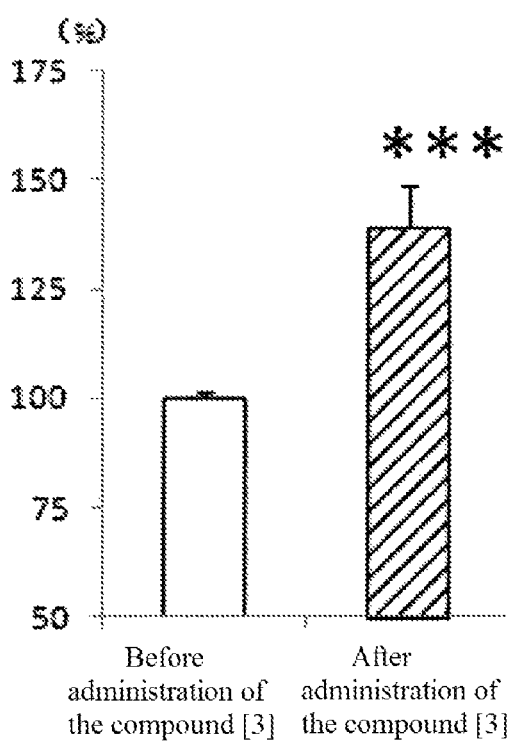

Comparison of Hemodynamics Before and after Administration of the Compound [3] of the Present Invention Wistar male rats were bred for a week and then anesthetized by inhalation of 3% isoflurane. Experiments were carried out in the same manner as in Test Example 1, and the compound [3] of the present invention was administered as a test compound at 0.1 mg/kg/min for 10 min, and the cardiac rate, left ventricular pressure, maximum +dP/dt, and maximum −dP/dt were measured for 20 heart beats every minute. The maximum +dP/dt or the maximum −dP/dt before administration was considered as 100%, and the value after administration was represented by a value (% representation) relative to the value before administration. The result is shown in FIG. 4. Data are shown as mean and standard deviation. Using n=3 rats, experiments were carried out.

Thus, the maximum +dP/dt (the left side in FIG. 4) and the maximum −dP/dt (the right side in FIG. 4) were significantly increased after administration of the compound [3] of the present invention.

Test Example 4

Figure 5:
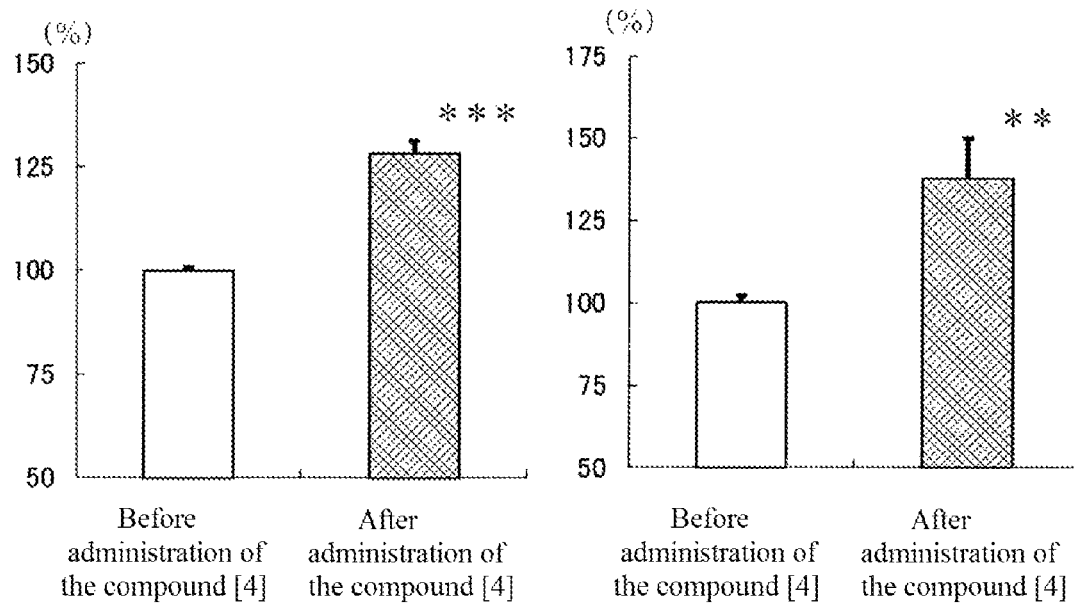
FIG. 5 shows graphs in which, when the compound [4] of the present invention is administered to normal rats, the maximum +dP/dt which is an index of contractile function before and after administration (the left side in FIG. 5) and the maximum −dP/dt which is an index of relaxing function before and after administration (the right side in FIG. 5) are compared. The  sign in FIG. 5 indicates that there is a significant difference between pre-administration of the compound [4] and post-administration at $p<0.01$. The * sign indicates that there is a significant difference between pre-administration of the compound [4] and post-administration at $p<0.005$.

Comparison of Hemodynamics Before and after Administration of the Compound [4] of the Present Invention Wistar male rats were bred for a week and then anesthetized by inhalation of 3% isoflurane. Experiments were carried out in the same manner as in Test Example 1, and the compound [4] of the present invention was administered as a test compound at 0.1 mg/kg/min for 10 min, and the cardiac rate, left ventricular pressure, maximum +dP/dt, and maximum −dP/dt were measured for 20 heart beats every minute. The maximum +dP/dt or the maximum −dP/dt before administration was considered as 100%, and the value after administration was represented by a value (% representation) relative to the value before administration. The result is shown in FIG. 5. Data are shown as mean and standard deviation. Using n=3 rats, experiments were carried out.

Thus, the maximum +dP/dt (the left side in FIG. 5) and the maximum −dP/dt (the right side in FIG. 5) were significantly increased after administration of the compound [4] of the present invention.

Test Example 5

About the Influence of the Following Comparative Compound [A] Described in Patent Document 1 (JP 2651043 B2), 1-[4-(diphenylmethyl)piperazinyl]-3-[4-(4-chlorophenyl)-4-hydroxy-piperidinyl]-2-propanol, on the Contractile and Relaxing Function of Normal Rats

[Chemical Formula 12]

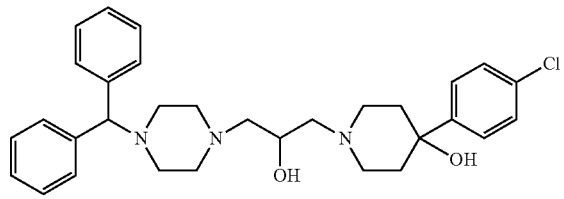

[A]

Figure 6:
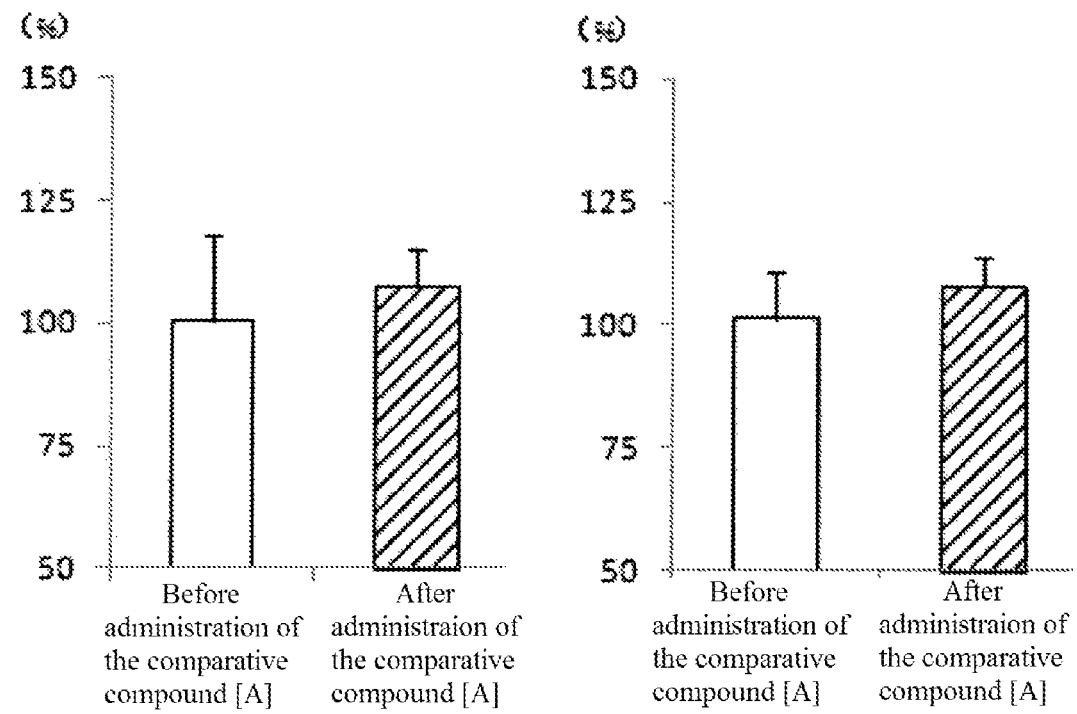
FIG. 6 shows graphs in which, when the comparative compound [A] is administered to normal rats, the maximum +dP/dt which is an index of contractile function before and after administration (the left side in FIG. 6) and the maximum −dP/dt which is an index of relaxing function before and after administration (the right side in FIG. 6) are compared.

Wistar male rats were bred for a week and then anesthetized by inhalation of 3% isoflurane. Experiments were carried out in the same manner as in Test Example 1, and the comparison comparative compound [A] was administered as a test compound at 0.1 mg/kg/min for 10 min, and the cardiac rate, left ventricular pressure, maximum +dP/dt, and maximum −dP/dt were measured for 20 heart beats every minute. The maximum +dP/dt or the maximum −dP/dt before administration was considered as 100%, and the value after administration was represented by a value (% representation) relative to the value before administration. The result is shown in FIG. 6. Data are shown as mean and standard deviation. Using n=3 rats, experiments were carried out.

Thus, as shown in FIG. 6, the maximum +dP/dt (the left side in FIG. 6) and the maximum −dP/dt (the right side in FIG. 6) tended to slightly increase after administration of the comparative compound [A], but significant changes were not observed as compared to those before administration.

Example 5

Comparison of the Contractile and Relaxing Function after Administration of the Compound [2], Compound [3], and Compound [4] of the Present Invention as Well as the Comparative Compound [A]

From the results of the tests carried out in Test Examples 1, 3, 4 and 5, the maximum +dP/dt (FIG. 7) and the maximum −dP/dt (FIG. 8) after administration of the compound [2], and compound [3], and compound [4] of the present invention as well as the comparative compound [A] were compared and examined.

Figure 7:
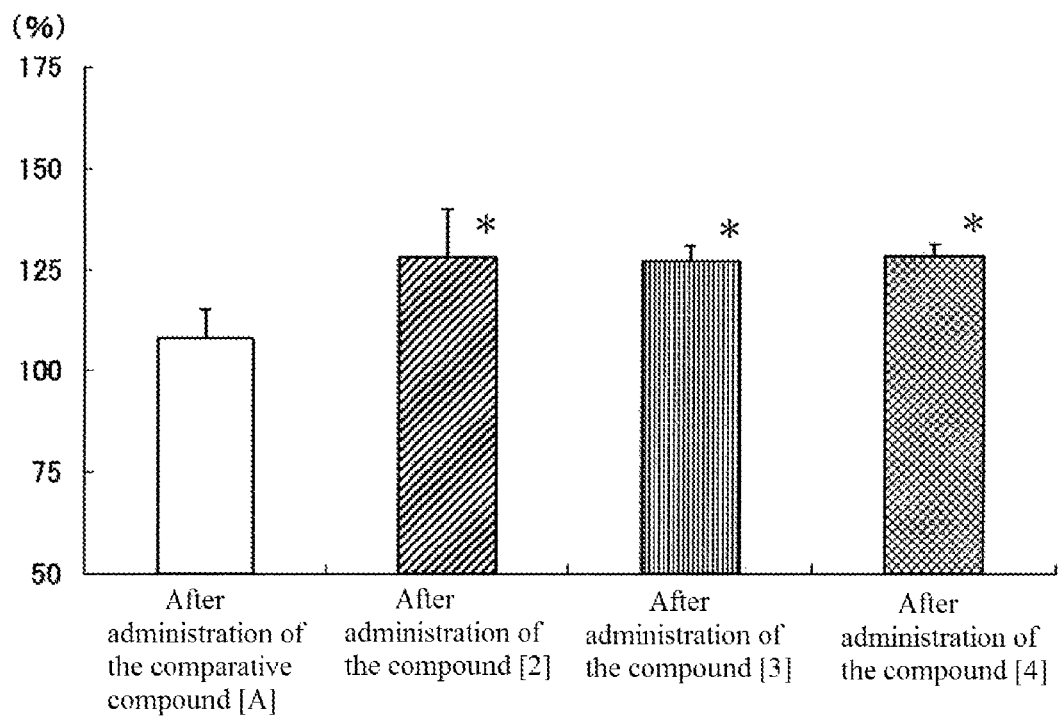
FIG. 7 shows a graph in which, when the compound [2], compound [3] or compound [4] of the present invention is administered to normal rats and when the comparative compound [A] is administered thereto, the maximum +dP/dt which is an index of contractile function after administration is compared. The * sign in FIG. 7 indicates that there is a significant difference between post-administration of the comparative compound [A] and post-administration of the compound [2], the compound [3] or the compound [4] at $p<0.05$.
Figure 8:
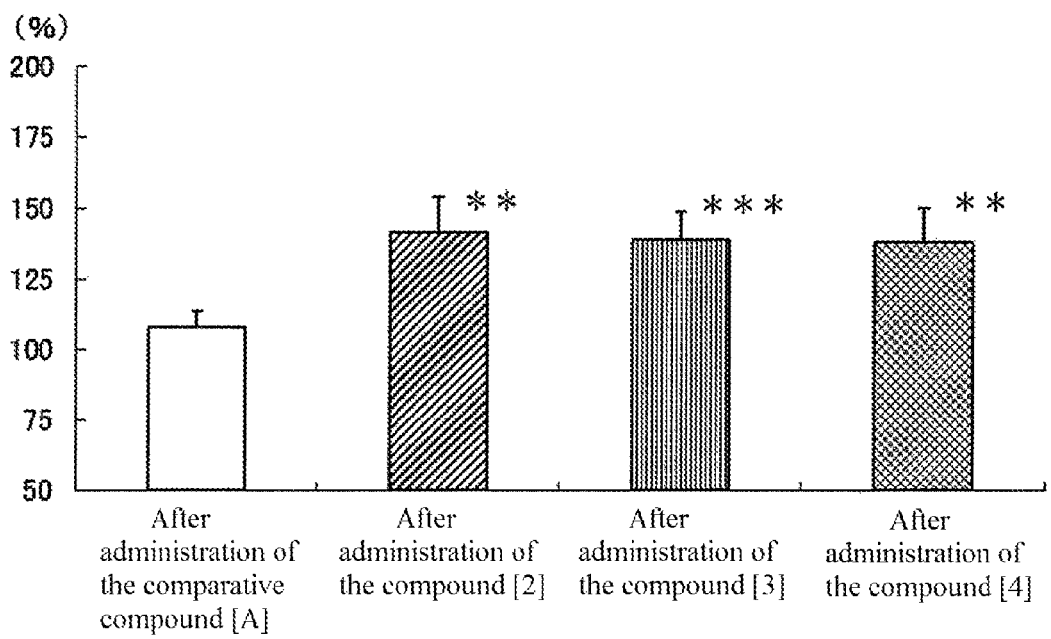
FIG. 8 shows a graph in which, when the compound [2], compound [3] or compound [4] of the present invention is administered to normal rats and when the comparative compound [A] is administered thereto, the maximum −dP/dt which is an index of relaxing function after administration is compared. The  sign in FIG. 8 indicates that there is a significant difference between post-administration of the comparative compound [A] and post-administration of the compound [2] or the compound [4] at $p<0.01$. The * sign indicates that there is a significant difference between post-administration of the comparative compound [A] and post-administration of the compound [3] at $p<0.005$.

Thus, as shown in FIG. 7, it was found that the maximum +dP/dt was significantly raised by the compound [2], compound [3], and compound [4] of the present invention as compared to that by the comparative compound [A], and also, as shown in FIG. 8, the maximum −dP/dt was significantly raised by the compound [2], compound [3], and compound [4] of the present invention as compared to that by the comparative compound [A].

From examples above, it was revealed that the compounds represented by the general formula [I] of the present invention had the strong effect of enhancing myocardial contraction and relaxation as compared to that of the comparative compound [A].

INDUSTRIAL APPLICABILITY

The present invention provides novel compounds, which are useful as an active ingredient of a pharmaceutical composition for treatment and/or prevention of heart failure, cardiogenic shock, tachyarrhythmia, myocardial infarction, or angina pectoris, and are useful in the pharmaceutical formulation industry and has industrial applicability.

The invention claimed is:

1. A diphenylmethyl piperazine derivative represented by the following general formula [I]:

[Chemical Formula 1]

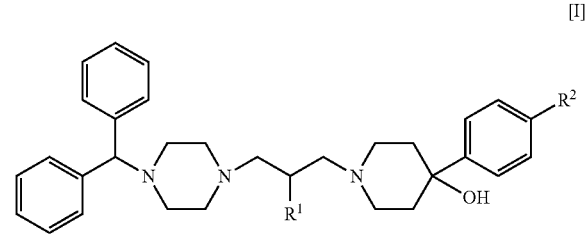

[I]

(wherein, $R^1$ represents a hydrogen atom or a hydroxy group, and $R^2$ represents a hydrogen atom, a halogen atom, a hydroxy group, an alkyl group having one to five carbon atoms, or an alkoxy group having one to five carbon atoms, excluding the case where $R^1$ is a hydroxy group and $R^2$ is a chlorine atom) or a pharmaceutically acceptable salt thereof.

2. The diphenylmethyl piperazine derivative or the pharmaceutically acceptable salt thereof according to claim 1, wherein the diphenylmethyl piperazine derivative is 1-[4-(diphenylmethyl)piperazinyl]-3(4-hydroxy-4-phenyl-piperidinyl)-2-propanol.

3. The diphenylmethyl piperazine derivative or the pharmaceutically acceptable salt thereof according to claim 1, wherein the diphenylmethyl piperazine derivative is 1-[4-(diphenylmethyl)piperazinyl]-3-[4-(4-chlorophenyl)-4-hydroxy-piperidinyl]propane.

4. The diphenylmethyl piperazine derivative or the pharmaceutically acceptable salt thereof according to claim 1, wherein the diphenylmethyl piperazine derivative is 1-[4-(diphenylmethyl)piperazinyl]-3-[4-hydroxy-4-(4-methylphenyl)-piperidinyl]-2-propanol.

5. A pharmaceutical composition comprising the diphenylmethyl piperazine derivative or the pharmaceutically acceptable salt thereof according to claim 1, and a pharmaceutically acceptable carrier.

6. A pharmaceutical composition comprising the diphenylmethyl piperazine derivative or the pharmaceutically acceptable salt thereof according to claim 2, and a pharmaceutically acceptable carrier.

7. A pharmaceutical composition comprising the diphenylmethyl piperazine derivative or the pharmaceutically acceptable salt thereof according to claim 3, and a pharmaceutically acceptable carrier.

8. A pharmaceutical composition comprising the diphenylmethyl piperazine derivative or the pharmaceutically acceptable salt thereof according to claim 4, and a pharmaceutically acceptable carrier.

* * * * *